United States Patent [19]

Goel

[11] Patent Number: 4,751,279
[45] Date of Patent: Jun. 14, 1988

[54] NOVEL POLYPHENATE SALTS OF TRIETHYLENE DIAMINE AND THEIR USE AS CATALYSTS FOR CURING A POLYEPOXIDE RESIN

[75] Inventor: Anil B. Goel, Worthington, Ohio

[73] Assignee: Ashland Oil, Inc., Ashland, Ky.

[21] Appl. No.: 57,475

[22] Filed: Jun. 3, 1987

[51] Int. Cl.$^4$ .................... C08G 59/68; C08G 65/10; B01J 31/00
[52] U.S. Cl. ........................................ 528/94; 502/167
[58] Field of Search ........................... 528/94; 502/167

[56] References Cited

U.S. PATENT DOCUMENTS

| | | | |
|---|---|---|---|
| 3,862,150 | 1/1975 | Bechara et al. | 528/94 |
| 4,161,575 | 7/1979 | Seymour et al. | 528/94 |
| 4,499,246 | 2/1985 | Tesson et al. | 528/94 |
| 4,526,940 | 7/1985 | Seymour et al. | 528/94 |
| 4,528,358 | 7/1985 | Kleeberg et al. | 528/94 |

*Primary Examiner*—Harold D. Anderson
*Assistant Examiner*—Dennis R. Daley
*Attorney, Agent, or Firm*—John F. Jones

[57] ABSTRACT

Novel solid, crystalline complexes of triethylene diamine and a polyphenol compound such as Bisphenol-A and the use of these complexes in the curing of polyepoxides and polyisocyanates are described.

4 Claims, No Drawings

NOVEL POLYPHENATE SALTS OF TRIETHYLENE DIAMINE AND THEIR USE AS CATALYSTS FOR CURING A POLYEPOXIDE RESIN

This invention relates to polyphenate salts of triethylene diamine, to a process for their preparation by reaction of a polyphenolic compound with triethylene diamine (DABCO) and to the use of these salts as polymerization catalysts.

Polyphenate salts of polyamines are known in the prior art (U.S. Pat. Nos. 2,829,175 and 3,076,576) and these materials have been used as latent or semi-latent curing agents for polyepoxide resins (U.S. Pat. No. 3,519,576). The polyphenate salts of triethylene diamine [also known as diaza(2.2.2) bicyclo octane or DABCO] have not hitherto been described. The use of polyphenate salts of DABCO as curing agents or catalysts in various polymerization reactions of polyepoxide resins and also polyisocyanates has not been previously disclosed in the prior art.

Although a variety of polyphenate salts of polyamines have been described in the foregoing patents; these are not useful catalysts in applications such as polyurethane and polyisocyanarurate polymerization reactions. The DABCO polyphenol catalysts of this invention are unique in that they not only promote curing of epoxy resins but in that they also are excellent catalysts for the polymerizations in which polyurethanes and polyisocyanurates are formed. Tertiary amines have been used as catalysts in the copolymerization reactions of polyisocyanates with polyols to give polyurethane polymers and as catalysts in the polymerization of polyepoxide resins cured with reactive hydrogen compounds such as amines, amido amines, carboxylic acids, and the like, tertiary amines are known to be corrosive and highly hygroscopic, thus sometimes when they are used as catalysts in polyurethane polymers, they cause undesired foaming problems.

It has now been discovered that triethylene diamine, a ditertiary amine, forms solid polyphenate complexes when mixed with polyphenols such as Bisphenol-A, 2,2'-biphenol, 4,4'-biphenol, resorcinol, 1,5-dihydroxynaphthalene, Bisphenol-F, 4,4'-sulfonyldiphenol, tetrachloro Bisphenol-A, Novolac resins and other types of phenol/formaldehyde resins. The polyphenate salts of triethylene diamine which are high melting crystalline solids are less corrosive and show low hygroscopicity when compared with triethylene diamine itself. The salts of this invention can be divided into fine powders of particle sizes smaller than 100 mesh and are easily dispersed in polyepoxide resins, polyamine and polyamide curatives, and have been found to have some solubility in poly(alkylene either) polyols. Despite the high melting points of these salts, they have the ability to cure epoxy resins either alone or in combination with other polyamine curatives at low-to-moderately elevated temperatures. The presence and availability of polyphenols in these salts help provide the rapid curing and improved physical properties in the final polyepoxide polymers. Thus, the 1:1 (mole ratio) Bisphenol-A/triethylene diamine salt has a melting point of about 240° C., cures a polyepoxide (liquid diglycidyl either of Bisphenol-A resin) at room temperature overnight and at 130° C. in about one minute when used at the level of about 20 parts by weight of the salt based on the weight of the resin. The resulting infusible thermoset polymer was found to have a Shore D hardness of 84.

The polyphenate salts of DABCO have been found to be excellent catalysts for the polymerization reactions of polyisocyanates. When used in small amounts as catalysts, these salts promote the rate of copolymerization of polyols with polyisocyanates (diisocyanates, polyisocyanates and also polyisocyanate prepolymers). The salts of this invention can be used in the form of finely divided powdered material dispersed in polyols or may be predissolved in the polyols. Most of the salts of this invention have been found to be somewhat soluble in chain extender polyols and long chain poly(alkylene ether) polyols used as crosslinkers in the formation of polyurethanes.

The polyphenate salts of DABCO of this invention have been found to catalyze the trimerization reaction of isocyanates and, particularly of aromatic isocyanates. Thus, when a small amount (1-2% by weight) of one of the salts of this invention is mixed with poly-aromatic isocyanates such as liquid modified methylene bis(phenyl isocyanate), trimerization of the isocyanate occurs to give a solid thermoset polymer in a few hours at room temperature. An exceedingly rapid rate of trimerization of liquid methylene bis(phenyl isocyanate) is observed when a small amount of an epoxide resin is added along with the salt of this invention to the mixture.

The polyphenate salts of DABCO are useful catalysts and curing agents for epoxide resins. The salts in the curing of polyepoxide resins may be used in amounts ranging from about 0.5 to 50 parts per hundred parts of polyepoxide and preferably from about 5 to 30 parts by weight. In the trimerization of polyisocyanate and also in the polyisocyanate/polyol copolymerization reactions, the salts of this invention may be used in the range of from 0.1 to 15% by weight, and preferably from 0.5 to 10% by weight based on the active ingredients.

The salts of this invention also promote the copolymerization of polyisocyanates with high melting solid polyols (such as pentaerythritol) which require long time to cure at high reaction temperatures (about 150° C. or so). In the trimerization of polyisocyanates small amounts of epoxide resins ranging from about 0.1 to 70% by weight of the total isocyanate/epoxide mixture improve the cure rate of the mixture significantly. Illustrative of this, when modified liquid methylene bis(phenyl isocyanate) containing 2% by weight of the Bisphenol-A/DABCO salt was mixed at room temperature with 3 weight percent of liquid diglycidyl ether of Bisphenol-A, a rapid polymerization with a strong exotherm occurred within 10 seconds to give a hard thermoset polymer having a Shore D hardness of 95. Similarly, a solution of liquid methylene bis(phenyl isocyanate) and the liquid diglylcidyl ether of Bisphenol-A in 1:1 weight ratio was mixed with 2% by weight of Bisphenol-A/DABCO salt and a polymer was obtained within one minute of mixing and after 10 minutes of postcuring of this polymer at 130° F. it was found to be tough with a Shore D hardness of 95.

The catalysts of this invention (polyphenate salts of DABCO) may be used in applications such as coatings, adhesives, composites, reinforced thermoset polymers, RIM (reaction injection molding), potting compounds and many others using polyisocyanates and polyepoxide polymers.

Epoxy resins or polyepoxides useful in the polymerization reactions which are catalyzed with the polyphenate/triethylene diamine salts of this invention include those disclosed in U.S. Pat. Nos. 2,500,600 and 2,324,483 which patents are incorporated herein by reference. Among the epoxy resins useful in this invention are the 1,2-epoxy compounds having an epoxide equivalence greater than 1, that is to say, compounds containing more than one group of the formula

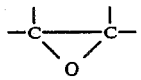

The 1,2-epoxide groups may be either terminal or inner ones. Particularly suitable terminal 1,2-epoxide groups are 1,2-epoxy ethyl or 1,2-epoxy propyl groups. The latter may be linked to an oxygen atom, that is to say, they are glycidyl ether or glycidyl ester groups. Compounds with inner epoxide groups usually contain the 1,2-epoxide group in an aliphatic chain or in a cycloaliphatic ring.

As epoxy compounds containing an inner 1,2-epoxy group there are suitable epoxidized diolefins, dienes, or cyclic dienes, such as 1,2,5,6-diepoxy hexane, 1,2,4,5-diepoxy cyclohexane, dicyclopentadiene diepoxide, dipentene diepoxide, vinyl cyclohexene diepoxide, epoxidized diolefinically unsaturated carboxylic acid esters, such as methyl-9,10,12,13-diepoxy stearate or the dimethyl ester of 6,7,10,11-diepoxyhexadecane-1,16-dicarboxylic acid. Furthermore, there may be mentioned epoxidized mono-, di-, or polyesters, and mono-, di-, or polyacetals containing at least one cycloaliphatic 5-membered or 6-membered ring, to which at least two 1,2-epoxidized groups are linked.

A widely used class of polyepoxides which can be used in the present invention are the epoxy polyethers obtained by reacting a halogen containing epoxide or dihalohydrin, such as epichlorohydrin, epibromohydrin, 3-chloro-1,2-epoxy octaine, and the like with either a polylhydric phenol or a polyhydric alcohol.

Polyisocyanates useful in this invention include organic isocyanates having at least two isocyanate groups per molecule. The polyisocyanates can be of low, high or intermediate molecular weight and can be any of a wide variety of organic polyisocyanates including ethylene diisocyanate, trimethylene diisocyanate, dodecamethylene diisocyanate, hexamethylene diisocyanate, hexamethylene diisocyanate trimer, tetraethylene diisocyanate, pentamethylene diisocyanate, propylene-1,2-diisocyanate, 2,3-dimethyl tetramethylene diisocyanate, butylene-1,2- diisocyante, butylene-1,3-diisocyanate, 1,4-diisocyanato cyclohexane, cyclopentene-1,3-diisocyanate, p-phenylene diisocyanate, 1-methyl phenylene-2,4-diisocyanate, naphthalene-1,4-diisocyanate, toluene diisocyanate, diphenyl-4,4'-diisocyanate, benzene-1,2,4-triisocyanate, xylene-1,4-diisocyanate, xylylene-1,3-diisocyanate, 4,4'-diphenylene methane diisocyanate, 4,4'-diphenylene propane diisocyanate, 1,2,3,4-tetraisocyanato butane, butane-1,2,3-triisocyanate, polymethylene polyphenyl isocyanate, and other polyisocyanates having an isocyanate functionality of at least two more fully disclosed in U.S. Pat. Nos. 3,350,362 and 3,382,215. Polyisocyanates which are polymeric in nature including isocyanate prepolymers of all types are included in this invention. Preferred are the aromatic polyisocyanates and prepolymers thereof.

Polyols useful in this invention in the production of polyurethanes include those having at least two hydroxyl groups per molecule and having equivalent weights falling in the range of from about 30 to 5,000. Specific types of polyols include butane diol, cyclohexane dimethanol, tripropylene glycol, amide diols, urethane diols, polyether polyols such as poly (tetramethylene ether) diols, poly (propylene ether) polyols, polyester polyols and the like.

Polyhydroxy polyethers are suitable polyols and preferably those having at least 2 hydroxyl groups per molecule. Polyhydroxy polyethers can be prepared by polymerization of epoxides such as ethylene oxide, propylene oxide, butylene oxide, tetrahydrofuran, styrene oxide, or epichlorohydrin either on their own or by chemical addition to other materials such as ethylene glycol, propylene glycol, trimethylol propanes pentaerythritol and 4,4'-dihydroxy diphenyl propane. Sucrose polyethers also may be used. Poly butadienes having hydroxyl groups as well as other known hydroxyl containing vinyl addition polymerized polymers can be used. Hydroxyl containing polyesters, polythioethers, polacetals, polycarbonates and polyesteramides of the types known for the formation of polyurethanes may also be used. Particularly useful polyols are the polyhydric alcohols including ethylene glycol, propylene glycol, trimethylene glycol, triethylene glycol, pentaethylene glycol, polyethylene glycol, 1,4-butane diol, diethyelen glycol, dipropylene glycol, 2,2-dimethyl-1,3-propanediol, hexamethylene glycol, 1,4-cyclohexane dimethanol, pentaerythritol, xylene alcohols, ethyl resorcinol, propyl resorcinol, 2,4-dimethyl resorcinol, 3,6-dimethyl-1,2,4-benzene triol, ethyl pyrogallol, 2,4-methyl-1,4-dihydroxy naphthalene, 3-methyl-1,4,5-naphthalene triol, dimethylol toluene, dimethylol xylene, bis-hydroxy ethyl and bis-hydroxy propyl ethers of resorcinol, catechol, and hydroquinones, 1,5-dihydroxy naphthalene, and 4,4'-isopropylidene-bisphenol, and the like and others.

This invention is further illustrated in the following representative examples.

EXAMPLE 1

A polyphenate salt of Bisphenol-A and triethylene diamine [DABCO which is also known as diaza (2.2.2) bicyclo octane] was prepared by mixing 11.2 g of triethylene diamine in 100 ml of diethyl ether with a solution of 22.8 g of Bisphenol-A in 100 ml of diethyl ether under continuous stirring. The white crystalline solid salt which precipitated immediately after the mixing occurred was isolated by filtration and was washed with two 30 ml portions of diethyl ether and the solid was then dried under reduced pressure to give 32.8 g of free-flowing solid (yield 96.5%). The solid product was found to have a melting point of 238°–240° C. Amine value analysis of the product showed it was a 1:1 salt of Bisphenol-A and triethylene diamine. Other polyphenate salts of polyphenolic compounds with DABCO were prepared in this manner.

EXAMPLE 2

This example demonstrates the use of the salt described in Example 1 as a curing agent for polyepoxide resins. A liquid diglycidyl ether of Bisphenol-A (16 g) was mixed with 4 g of the powdered salt of Bisphenol-A/triethylene diamine having a particle size smaller than 100 mesh. The resulting pasty mixture was divided into two parts, one part was held at room temperature to determine the pot life of the mixture and the other part was heated at 122° C. The heated sample cured to a solid resin in 1.1 minutes. This resin was found to be an infusible thermoset polymer having a Shore D hardness of 85. The sample maintained at room temperature became solid in less than two days.

EXAMPLE 3

A 4,4'-biphenol/DABCO (1:1 molar ratio) salt (melting point greater than 260° C.) prepared by following the procedure of Example 1 was mixed with the liquid diglycidyl ether of Bisphenol-A in 20% by weight of the salt based on the weight of the polyepoxide. The procedure of Example 2 was followed and the sample held at room temperature cured in about two days to yield a hard polymer, whereas the sample heated at 125° C. cured in 1.1 minutes to give a thermoset polymer having a Shore D hardness of 84.

Example 4

This example demonstrates that polyphenate salts of triethylene diamine can be used as cure rate accelerator for polyepoxide resin curing with polyamines which have poor activity in curing epoxide resins. A curative composition was prepared by mixing 55 parts by weight of poly(propylene oxide) triamine (molecular weight of 3100), 25 parts by weight of poly(propylene oxide) diamine (molecular weight of 400) and 20 parts by weight of the Bisphenol-A/triethylene diamine salt described in Example 1. This curative was filled with 30% by weight of dry talc. The resulting material was mixed in a 1:1 weight ratio with an epoxy resin containing 70 parts by weight of liquid diglycidyl ether of Bisphenol-A, 10 parts by weight of a carboxylic acid terminated butadiene/acrylonitrile (18% by weight of acrylonitrile in the polymer) rubber, 8 parts by weight of talc and 2 parts by weight of fumed silica. The resulting mixture of epoxy resin and curative produced a pasty material which had room temperature open time of greater than one day and a cure time at 120° C. of three minutes. In contrast, when the curative composition having no polyphenate/triethylene diamine salt in it was used the curing time at 120° C. for the mixture was more than one hour. The epoxy adhesive which contained the curative containing the Bisphenol-A/triethylene diamine salt in the curative described above was tested as a structural adhesive towards sheet molding compound (SMC). The lap shear samples for 1"×1" SMC sheets bonded together using this adhesive composition in which the adhesive covered one square inch of bonded area between two substrates with a glue line thickness of 30 mils and postcured at 140° C. for 30 minutes gave lap shear strengths (ASTM D-1002) in the range of 300 to 500 psi with fiber tear in all cases.

EXAMPLE 5

This example demonstrates that the polyphenate salts of DABCO can be used as polyurethane catalysts in the copolymerization reactions of polyisocyanates and polyols. To poly(propylene oxide) tetraol (hydroxy equivalent weight of 113) (40 g) was mixed 0.4 g of the Bisphenol-A/triethylene diamine salt described in Example 1. An 8 g portion of this mixture was blended at room temperature with 8.4 g of liquid methylene bis(phenyl isocyanate) (NCO functionality of 2.1 per mole with equivalent weight of 144). Gelation occurred in about 3 minutes to give a hard, solid polymer. In comparison, when the polyol and polyisocyanate were mixed together in the absence of the salt catalyst of this invention, the mixture remained ungelled for more than one hour. In another experiment, 8 g of the tetraol was mixed with 8.4 g of the polyisocyanate. To this mixture was added 0.1 g of solid, powdered Bisphenol-A/triethylene diamine salt. Polymerization occurred within three minutes to give a gelled, solid polymer.

EXAMPLE 6

This example demonstrates the use of polyphenate salts of DABCO as catalyst in the polyurethane polymerization involving solid polyols which are known to have poor reaction towards polyisocyanates. The liquid methylene bis(phenyl isocyanate) described in Example 5 (7.5 g) was mixed 2.2 g of powdered pentaerythritol. The resulting mixture was heated at 140° C. for 30 minutes during which time the mixture remained ungelled. When a similar mixture to which 0.1 g of the Bisphenol-A/triethylene diamine catalyst was also added was heated at 110° C., gelation occurred within 3 minutes to give a solid polymer.

EXAMPLE 7

A resorcinol/triethylene diamine salt was prepared by the procedure of Example 1. To 0.35 g of this salt was added 8 g of poly(propylene oxide) tetraol (molecular weight of 450). To the resulting mixture was added 8.4 g of liquid methylene bis(phenyl isocyanate) at room temperature. Polymerization of the resulting mixture resulted within 3 minutes of the time of mixing to give a thermoset polymer.

EXAMPLE 8

This example demonstrates that the polyphenate salts of DABCO can be used as isocyanate trimerization catalysts to give tough, hard isocyanate polymers. To liquid methylene bis(phenyl isocyanate) (15 g) was added 0.6 g of Bisphenol-A/triethylene diamine catalyst. A part of this mixture was kept at room temperature and the other part was heated at 120° C. The heated sample polymerized in 3 minutes to give a thermoset polymer. The sample maintained at room temperature gelled overnight to a solid polymer. In a similar experiment when a small amount (0.3 g) of liquid diglycidyl ether of Bisphenol-A was added at room temperature to a sample of 8 g of liquid methylene bis(phenyl isocyanate) containing 0.2 g of Bisphenol-A/DABCO catalyst, a rapid polymerization occurred within 15 seconds to give a thermoset polymer. This polymer after postcuring at 130° C. for 15 minutes was found to have a Shore D hardness of 95.

EXAMPLE 9

To a mixture of 4 g of the liquid diglycidyl ether of Bisphenol-A and 4 g of liquid methylene bis(phenyl isocyanate) was added 0.2 g of the catalyst described in Example 1. Rapid polymerization occurred within one minute to give a solid polymer which after being postcured at 130° C. for 15 minutes was found to have a Shore D hardness of 95.

EXAMPLE 10

The procedure of Example 8 was followed using 0.3 g of liquid diglycidyl ether of Bisphenol-A, 8 g of liquid methylene bis(phenyl isocyanate) and 0.2 g of resorcinol/DABCO salt. The resulting mixture was heated at 110° C. A rapid polymerization occurred within 10 seconds to give a thermoset polymer having a Shore D hardness of 96. The infrared spectrum for this polymer in nujol mull showed a strong band at 1705 cm$^{-1}$, showing the formation of isocyanurate groups in the polymer.

EXAMPLE 11

This example demonstrates the use of the Bisphenol-A/triethylene diamine salt as catalyst in a reaction injection molding (RIM) composition.

A solution of 15 g. of propylene glycol, 15 g of dipropylene glycol, 15 g of poly(propylene oxide) triol (molecular weight 4500) and 0.45 g of the Bisphenol-A/triethylene diamine salt catalyst was prepared and degassed on a rotary evaporator. The resulting solution was mixed with 90 g of degassed liquid methylene bis(phenyl isocyanate) (NCO functionality of 2.3 per molecule) and the mixture was poured into a mold kept at a temperature of 100° C. prepared by placing two silicone mold release coated parallel glass plates adjacent one another and held apart by ⅛ inch thick spacers. The mixture polymerized within two minutes in the mold to give a solid sheet which was post cured at 130° C. for 30 minutes.

The resulting polymer sheet was found to have a notched izod impact strength (ASTM D-256) of 1.1 foot pounds per inch of notch, a heat distortion temperature (ASTM D-648) of 115° C., flexural strength (ASTM D-790) of 13,791 psi and a flexural modulus of 337,349 psi.

I claim:

1. The process for curing a polyepoxide resin comprising mixing a polyepoxide with from about 0.5 to 50 parts by weight based on the weight of the polyepoxide of a solid complex of trirthylene diamine and a component selected from the group consisting of Bisphenol-A, 2,2'-biphenol, 4,4'-biphenol, resorcinol, 1,5-dihydroxynaphthalene, Bisphenol-F, 4,4'-sulfonyldiphenol, novalacs and other phenol/formaldehyde resins and curing at a temperature in the range of from about room temperature about to 130° C.

2. The proces of claim 1 wherein the polyepoxide is a liquid diglycidy ether of Bispenol-A and the complex is the reaction product of Bisphenol-A and triethylene diamine.

3. The process of claim 1 wherein the polyepoxide is a liquid diglycidyl ether of Bisphenol-A and the complex is one resulting from the reaction of 4,4'-biphenol and triethylene diamine.

4. The process of claim 1 wherein the polyepoxide is a liquid diglycidyl ether of Bisphenol-A and the complex is one resulting from the reaction of resorcinol and triethylene diamine.

* * * * *